United States Patent [19]
Lex et al.

[11] Patent Number: 5,760,890
[45] Date of Patent: Jun. 2, 1998

[54] DEVICE FOR MEASURING OPTICAL CHARACTERISTIC QUANTITIES OF TRANSPARENT MATERIALS

[75] Inventors: Konrad Lex, Königsdorf; Peter Schwarz, Geretsried; Ralf Zellner, Icking, all of Germany

[73] Assignee: BYK-Gardner GmbH, Geretsried, Germany

[21] Appl. No.: 707,993

[22] Filed: Jul. 12, 1996

[30] Foreign Application Priority Data

Jul. 13, 1995 [DE] Germany .............. 295 11 344.8

[51] Int. Cl.[6] ..................................... G01J 1/04
[52] U.S. Cl. .................. 356/236; 356/239; 250/228
[58] Field of Search ............................ 356/236, 239, 356/336, 338, 339, 343; 250/228; 359/707–711

[56] References Cited

U.S. PATENT DOCUMENTS

| | | | |
|---|---|---|---|
| 3,788,744 | 1/1974 | Friedman et al. | 356/336 |
| 5,098,187 | 3/1992 | Judge | 356/236 |
| 5,190,163 | 3/1993 | Anzai et al. | 356/236 |

FOREIGN PATENT DOCUMENTS

| | | | |
|---|---|---|---|
| 0075537 | 4/1988 | Japan | 356/236 |
| 0314445 | 12/1988 | Japan | 356/236 |
| 6123702 | 5/1994 | Japan | 250/228 |

*Primary Examiner*—Hoa Q. Pham
*Attorney, Agent, or Firm*—Ohlandt, Greeley, Ruggiero & Perle

[57] ABSTRACT

The invention provides a device for measuring characteristic quantities of an at least partially transparent sample, comprising: an illumination component including a light source (1) which emits light in a predetermined wavelength range and which is arranged such within this illumination component that the light substantially propagates along a predetermined optical axis, a sample reception space provided between this illumination component and a measuring component and arranged such with respect to this optical axis that the light which emerges from the light source first passes a sample located within that sample reception space and then enters this measuring means, a measuring component including a substantially closed measuring space having an opening through which this optical axis extends and through which the light enters after having passed the sample, and which also includes a photodetector component (2) being sensitive at least within this predetermined wavelength range, including at least two detectors, namely a first detector (4) arranged in the optical axis (3) of the illumination component and a second detector (5) arranged in a predetermined radial distance from this optical axis.

18 Claims, 4 Drawing Sheets

DEVICE FOR MEASURING OPTICAL CHARACTERISTIC QUANTITIES OF TRANSPARENT MATERIALS

BACKGROUND OF THE INVENTION

This invention is related to a device for measuring characteristic quantities of an at least partially transparent sample.

Transparent products such as glass, transparent foils and the like are applied in a variety of fields. The optical characteristics play an essential role regarding the field of application. For example, glass plates and foils used for greenhouses are required to have a high transmission. A foil used for packing, however, should make visible the contents in a possibly clear and undull way.

A merely subjective observation of the optical quality of the material as nowadays often performed both in the development and in the manufacturing exhibits the essential disadvantage, that these observations cannot at all or only with rough grading be quantified, so that a comparison of the results is only possible within narrow limits.

Therefore in research and development devices are used to measure the degree of transmission of transparent materials, for example. These devices, however, exhibit the disadvantage that they are very costly and they do not allow a determination different optical characteristic quantities which are required for the judgement of the optical qualtity of the products.

SUMMARY OF THE INVENTION

Thus, it is an object of the present invention to provide a device by means of which optical characteristic quantities of transparent materials may be reliably and reproducably detected.

According to the invention this object is solved by the device as described below.

Preferred embodiments of the invention are also described below.

The inventive device uses an illumination means which is arranged such that the emitted light which preferably covers the wavelength range of visible light, propagates along a predetermined optical axis. The light passes a sample reception space wherein the sample is arranged and then impinges into a measuring means wherein a first detector on this optical axis and a second detector distant from this optical axis are arranged.

Preferably the spectral composition of the emitted light corresponds to a normed composition such as the kind of light C normed by the ASTM.

By means of the first detector the fraction of the light is measured which straightly passes through the sample. By means of the second detector the fraction of the light is measured which is deflected within an angle range i.e. 5° or less, corresponding to the arrangement of the second detector when passing through the sample. If the second detector is arranged in close distance to the first detector, the deflection of the light into a narrow angle range is determined, if, however the distance is enhanced, then the deflection of the light for a large angle is detected.

The first and the second detectors are preferably located in a measuring space which exhibits an opening, which the light enters along the optical axis. The sample reception space is arranged in front of this opening.

Very preferably, the measuring space has a spherical surface in its interior, i.e. precisely spoken the internal surface of a sphere, which preferably has a white coating. Such a sphere is known as Ulbricht-sphere in the field of optical measuring devices. In the following the term surface is always to be understood as internal surface of this measuring space.

Preferably a third detector is provided which also has a distance to the optical axis, which however is arranged such that it substantially only detects the light reflected from the surface of this measuring space, i.e. preferably from the Ulbricht-sphere.

By means of this arrangement a particular desire of the present invention is achieved, namely to be able to simultaneously measure both the large angle dispersion (haze) and the small angle dispersion (clarity). In this measuring arrangement the second detector is arranged in such a distance to the optical axis that the small angle dispersion, i.e. an angle deviation up to 2.5° of the light passing through the sample, is detected. The light deflected by an angle larger than 2.5° is detected neither by the first nor by the second detector, but is reflected by the internal surface of the measuring space. This reflected light is detected by the third detector in accordance with the principle of the Ulbricht-sphere.

Thus, in this embodiment the first detector detects the light passing straightly through the sample, the second detector detects a quantity of light which is a measure of the small angle dispersion, and the third detector detects the quantity of light which is a measure of the dispersion of the light being larger than the exemplarily chosen angle deviation of 2.5° of the second detector. Thus, the inventive measuring device allows a precise statement about small angle dispersion and large angle dispersion is to be made by performing a single measurement.

In a preferred embodiment of the invention a movable covering means is provided within the measuring space by means of which the first and second detectors may be covered. If the preferred Ulbricht-sphere is used as measuring space, this means that a white coated sphere surface sector is provided which is movable from a first position, wherein the openings in the surface of the sphere for the first and second detectors are uncovered, into a second position, wherein the openings in the surface of the sphere for the first and second detectors are covered.

In this covered state only the third detector is still able to measure. In this position all of the light which passes through the sample and enters into the measuring space is reflected by the surface of the sphere. Consequently, the quantity of light measured by the third detector is a measure of the total transmission behavior of the sample.

Thus, by use of this embodiment of the inventive device a plurality of detailed statements about the optical behavior of the respective sample can be made:

First the measurement is performed with closed cover and then makes it possible to judge the total transmission behavior. As mentioned, this is a value which is of great importance for foils or glass plates of greenhouses, for example.

Thereafter the cover is opened and the measurement is performed again. In this case the first detector detects the quantity of light passing linearly through the sample, the second detector detects the small angle dispersion, and the third detector detects the quantity of light which is deflected by larger angles. If the quantity of light detected by the second and third detectors is small, this means that the sample lets the light pass in an extensively undistorted manner. For example, this applies to a glass which is usually used as window glass.

If the quantity of light measured by the second detector is large, and the quantity of light measured by the third detector is small, however, then predominantly small angle dispersion is present, which means that a product packed within a corresponding foil, for example, is well visible, however, the clarity is deteriorated.

If the quantity of light measured by the third detector is large, and the quantity of light measured by the second detector is small, this means that predominantly large angle dispersion is present, i.e. that the material is not suited as transparent packing material, for example.

Thus, a single measuring device suffices for judging the essential optical characteristics of the sample. Moreover, precise reproduceable numerical values for the judgement of the single samples are provided, so that a comparison of different materials in the development is made possible and the maintenance of quality standards in the production can be secured.

In another preferred embodiment the first detector is arranged such in relation to the optical axis that a reflected fraction of an impinging beam of light is no longer reflected into the measuring space, particularly into the Ulbricht-sphere, and consequently can no longer disturb the measurement of large angle dispersion. This is achieved by inclining the detector at the end of a short channel with respect to the optical axis such that the light is reflected onto the wall of the channel and is absorbed by an accordingly designed wall.

Preferably, also the second detector is arranged such that a reflection into the sphere and consequently a deterioration of the haze measurement is avoided. This is preferably achieved by arranging the second detector at the end of a channel which exhibits a short extension in the vertical direction with respect to the optical axis.

In accordance with another preferred embodiment a modulation means for modulating the light beams and a means for detecting the signals outputted by the detectors in a way tuned to the modulation are provided. In accordance with this measure the influence of interference light, for example of artificial light of the measuring space having power supply frequency, can be suppressed when using an appropiate frequency, so that the device can be used in an exposed way, i.e. with uncovered sample space. In order to avoid that a part of the incident interference light is modulated, it is useful to provide the modulation means in the illumination means in a dark region. Preferably the modulation means may be a mechanical chopper aperture which interrupts and transmits the light beam in accordance with a predetermined time scheme.

According to another preferred embodiment a reference measuring means for measuring a reference beam of the illumination means is provided. Accordingly, not only the measuring precision of the device is enhanced; by referring the measuring signals to the signal of the reference measuring means also a self-adjustment regarding timely increasing changes of the characteristics of the illumination means is given in a simple way. This improves the userfriendliness. If the reference measuring means is preferably provided at the illumination means it can even then be used if there is a sample present between the illumination means and the photodetector means or the Ulbricht-sphere, respectively.

In another preferred embodiment the reference measuring means include a partially transparent mirror which deflects a part of the light in the illumination means from the beam leading to the sample and directs it to a detector outputting the signal of the reference measuring means. This arrangement is very simple and reliable.

In accordance with another preferred embodiment on one hand the illumination means and on the other hand the Ulbricht-sphere with the photodetector means are attached to a common base plate, which substantially runs in parallel to the optical axis via a respective column. It is experienced that this construction is simple and reliable. If the attachment is performed in a detachable fashion, the illumination means or the Ulbricht-sphere having the photodetector means, respectively, can be individually detached or exchanged for repair or maintenance. Particularly, this arrangement is suited to realize a spacious and very well accessible arranged sample space, because the columns provide a predetermined distance from the base plate connecting on one hand the illumination means and on the other hand the Ulbricht-sphere to the photodetector means.

In accordance with another preferred embodiment a user control device is provided at the illumination means which may also comprise display elements. This arrangement is not only simple, because a separate design of the user control device is not necessary, it also allows a position of the user control device which is comfortable for the user, for example in the above mentioned arrangement of the illumination means on a column which preferably vertically extends from the base plate arranged below to the illumination means located above.

In accordance with another preferred embodiment the partially transparent mirror is arranged such that it directs the reference beam to the base plate, and the reference measuring means is arranged at least substantially in parallel to the column of the illumination means. This very simple arrangement allows to quasi integrate the reference measuring means in or at the column and to provide it preferably in a common cover together with the column. Thus, the arrangement gets compact and clearly laid out and userfriendly for a user working with samples which under circumstances are difficult to manage.

In another preferred embodiment the chopper aperture is arranged in the direction to the base plate, i.e. supported between the illumination means and the base plate, leading to advantages comparable to the ones described above for the measuring means. Preferably both the modulation means having the chopper aperture and the reference measuring means are integrated in the column and provided in a common cover.

Furthermore it is preferable to arrange the detecting regions of the first and second detectors in a symmetrical way with respect to a rotation around the optical axis, i.e. circularly in the first detector and at least substantially in form of a circular ring in the second detector. As shown in the embodiment, the limitation "substantially" may mean that small webs pass through the circular ring which for mechanical static reasons connect the region between the circle and the circular ring and the region outside the circular ring to each other. The circular ring design provides the advantage that a material structure, which causes a directed angle deflection, does not deteriorate the measuring result. For such materials also a rotation of the material around the optical axis does not effect any change of the measuring result.

Preferably, a surface of the detector means in this intermediate region pointing to the illumination means may at least to a major part be formed by an inclined area, i.e. the plane of the area is not vertical to the optical axis in order to diminish back reflexions, particularly into the Ulbricht-sphere.

Instead of using an inclined detector area for the region(s) of the detector(s), for which the inclination incurs problems, preferably a light inlet channel having a small extension in the plane vertical to the optical axis and a relatively large extension in parallel to the optical axis is provided. Also by this means the reflection of the light impinging onto the detector areas in the Ulbricht-sphere may be effectively diminished.

BRIEF DESCRIPTION OF THE DRAWINGS

A preferred embodiment of the invention will now be explaneed with reference to the drawing. In the Figures are.

DESCRIPTION OF THE PREFERRED EMBODIMENTS

The embodiment explained in the following uses the three optical characteristic quantities transmission, haze and clarity for optically characterizing transparent samples.

Herein the quantity transmission or total transmission expresses the relation of the light intensity transmitted through the sample to the light intensity impinging onto the sample. Thus it corresponds to the optical perception "bright/transparent" in the characterization by the human eye.

The quantity haze corresponds to the fraction of the light intensity transmitted under directional deflection with respect to the total transmitted light intensity and will therefore be referred to as large angle dispersion. This quantity corresponds to the optical perception "dull/milky" in the characterization by the human eye. The haze of a transparent material may, for example, be caused by statistically distributed embedded particles, bubbles or other material inhomogenities which lead to a substantially statistical deflection of the impinging light by various, also large angles. Also a corresponding surface roughness may exhibit this effect. According to ASTM D 1003 the haze characterizes the percentage of the light which deviates by more than 2.5° from the irradiated light bundle.

The quantity clarity serves for characterizing a material property, where a noticeable part of the light beams is transmitted with very small angular deflections, and is therefore be referred to as small angle dispersion. This may occur for slightly uneven surfaces, wherein the unevenness exhibits only very small difference angles in comparison to an ideal plane parallel geometry. Arithmetically the quantity clarity may be defined as quotient of the difference of the light intensity transmitted without any deflection and the light intensity slightly deflected as mentioned above and the sum thereof. The smaller the tendency of the sample to slightly deflect the light in the above described manner, the larger is the value of clarity. According to ASTM D 1003 the clarity has to be determined under a deviation which is smaller than 2.5°.

Figure 1:
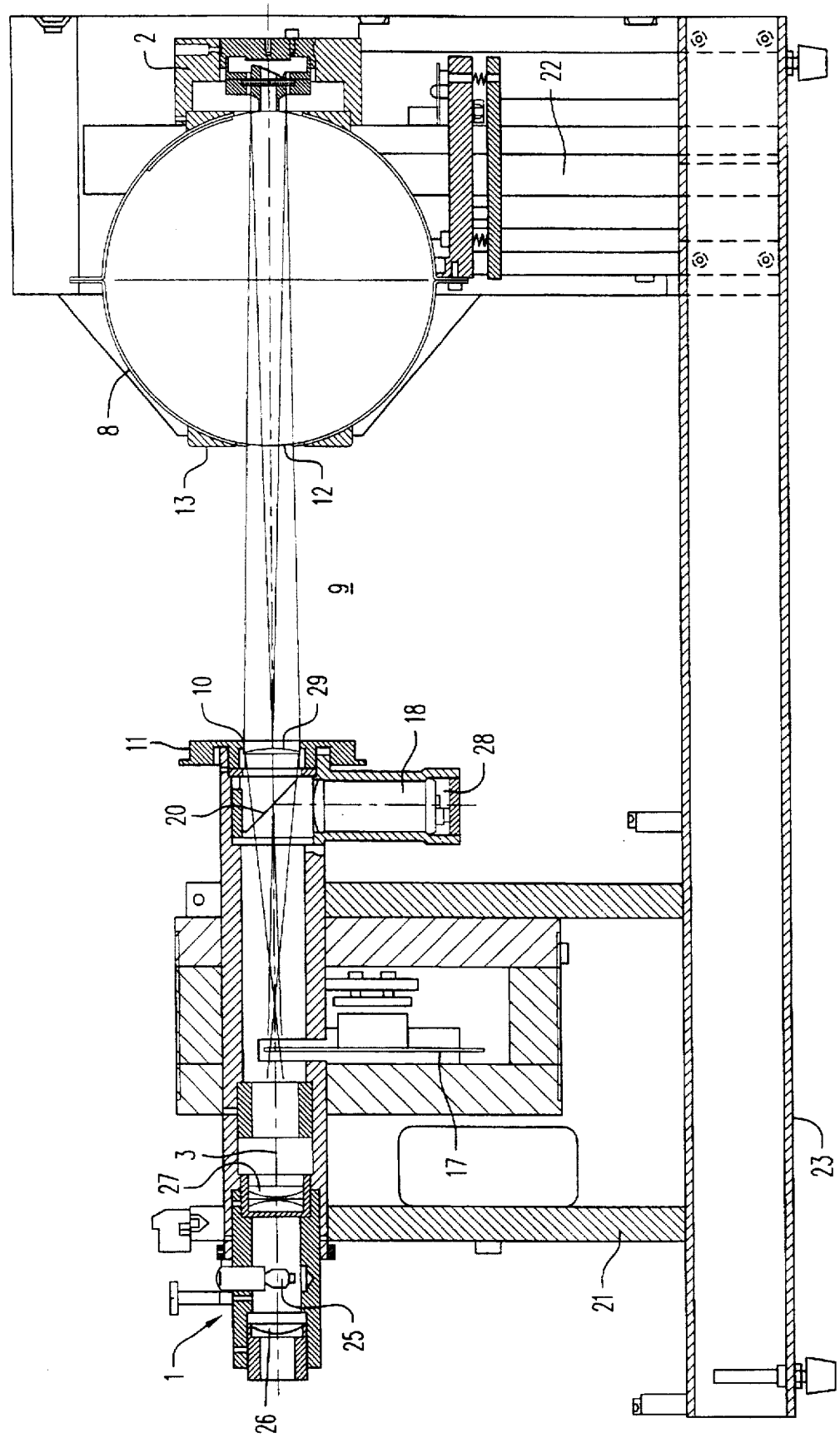
FIG. 1 a partial sectional sideview of an inventive device.

In the embodiment illustrated in the drawings, in the left region of FIG. 1 an illumination means 1 attached to a base plate 22 via a column 21 is shown, wherein a halogen lamp 25 as a light source emits visible light. Left hand of the halogen lamp 25 there is a reflector 26 which symmetrically with respect to an optical axis 3 reflects the light onto a condensor 27.

17 denotes a rotatable chopper aperture which modulates the light of the illumination means 1 by successive masking and passing of the light coming from the condenser 27. A part of the modulated light is reflected by a partially transparent mirror 20 downwards to a reference measuring means 18 comprising a reference detector 28. An outlet opening of the illumination means 1 is denoted by 10 and includes a focusing lense 29 which also serves for protection of the illumination means. Moreover, an annex 11 is formed as a first boundary of a sample space.

Also centered on the optical axis 3 there are an Ulbricht-sphere 8 and a photodetector means 2, which are attached to the base plate 23 via an adjustable supporting means 22. The Ulbricht-sphere 8 comprises an inlet opening 12 and an annex 13. Between the annexes 11 and 13 a continous sample space 9 is provided, which is open to both remaining horizontal sides and in the upward direction, and which is limited by the base plate 23 in by the height of the columns 21 and 22 relatively wide allocated distance.

Figure 2:
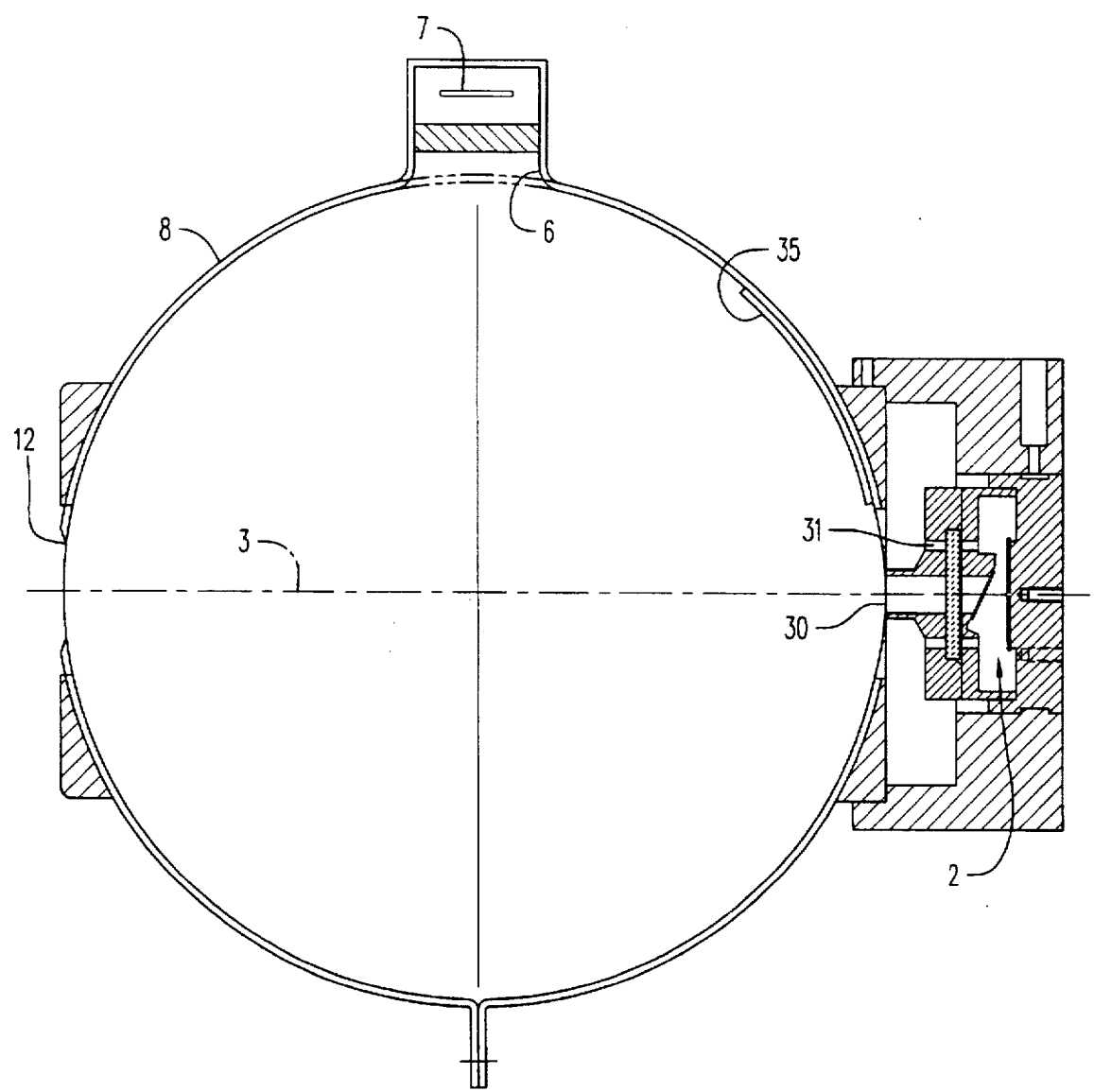
FIG. 2 a sectional view of the measuring device of the embodiment according to FIG. 1.
Figure 3:
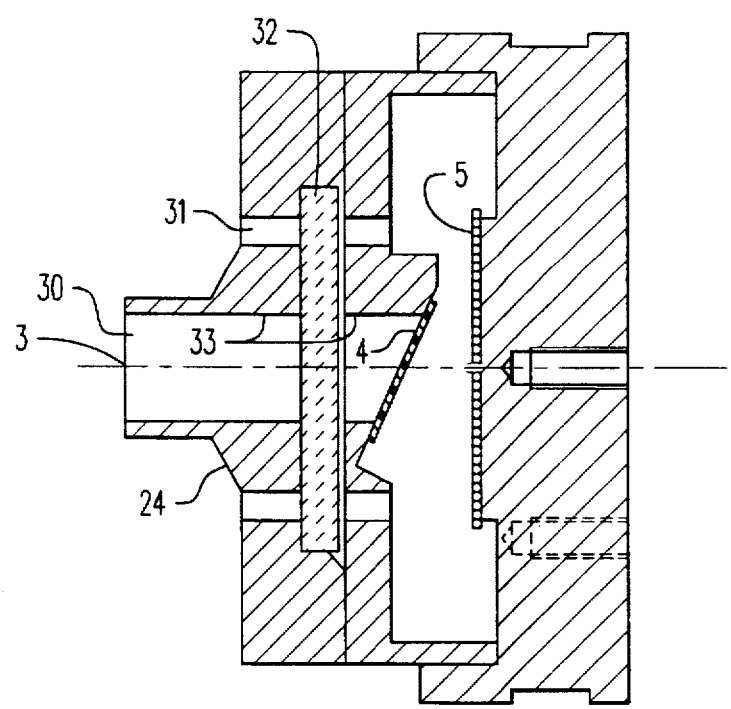
FIG. 3 a sectional view of a photodetector means of the embodiment according to FIG. 1.
Figure 4:
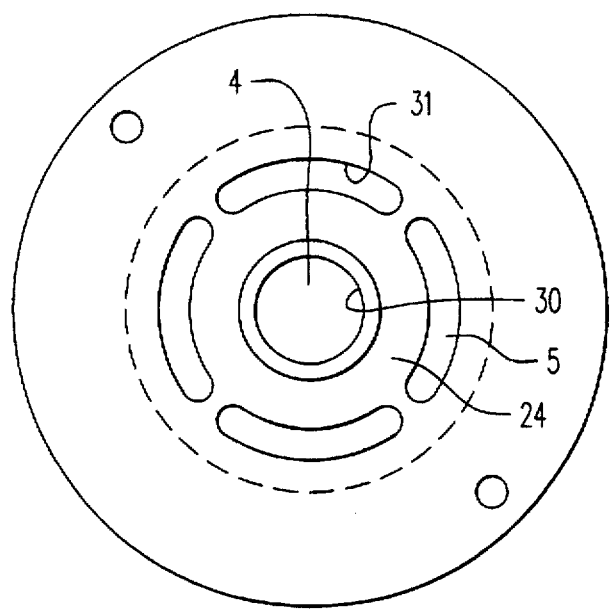
FIG. 4 a sideview of the photodetector means of the embodiment according to FIG. 1 from the side of an Ulbricht-sphere.

The construction of a photodetector means 2 arranged on the optical axis of the inlet opening 12 and opposite to the Ulbricht-sphere 8 is shown in FIG. 2 in detail. Here 4 denotes a first detector and 5 denotes a second detector. The first detector 4 detects the light from the Ulbricht-sphere 8 in a region which is defined by opening 30 towards the Ulbricht-sphere. The second detector 5 detects the light in a region which is defined by openings 31 towards the Ulbricht-sphere 8. As becomes apparent from FIGS. 2 and 4, the opening 30 has a circular cross section, whereas the openings 31 together form a circular ring cross section which is interrupted by four webs forming circular ring segments. In this embodiment these webs are required in order to keep the section of the photodetector means 2 between the opening 30 and the openings 31 from the section (in radial direction) outside the openings 31. A heat protection filter 32 is arranged such that it extends in the openings 31 and in the opening 30 so that light impinging onto detectors 4 and 5 has passed the heat protection filter 32.

Moreover it is apparent, that the first detector 4 is inclined with respect to the optical axis 3 in order to direct a reflected fraction of the impinging light to a light absorbing wall 33 which is a part of the area defining the opening 30.

Furthermore, a surface of the section of the photodetector means 2 directed to the Ulbricht-sphere between the opening 30 and the openings 31 is to a major part formed of such a bevelled area 24 that the light beams which substantially impinge in the direction of the optical axis 3 are not reflected back into the Ulbricht-sphere 8, as may be seen in comparison to FIG. 1.

The openings 31 have in width, i.e. in a plane which is vertical to the optical axis, only a small extension and are in comparison thereto relatively long, the length being measured in parallel to the optical axis. This measurement also serves to minimize reflections of the light from the detector surface back into the Ulbricht-sphere.

In the upper region of the Ulbricht-sphere there is a third detector 7 arranged in an opening 6, as may be obtained from FIG. 2. In the embodiment the arrangement is such that the light sensitive area of the detector is substantially vertical with respect to the optical axis. Moreover, the light sensitive area is moved backwards with respect to the surface of the sphere.

In FIG. 1 it is indicated that the Ulbricht-sphere 8, the photodetector means 2 and the column 22 are acommodated in a common cover. In the same way the illumination means 1 including the chopper aperture 17 and the reference measuring means 18 having the detector 28 are accomodated in a common cover. To this purpose the chopper aperture 17 and the reference means 18 are oriented downwards to the base plate 23 in order to achieve an arrangement which is as compact as possible.

As also shown in FIG. 2, there is a cover area 35 the form of which is adapted to the form of the surface of the sphere and which is supported in such a movable manner (not shown) that it may be moved from a first position as illustrated in FIG. 2 to a second position wherein it covers the openings 30 and 31. The cover area 35 is coated in white at its side which is directed to the light inlet opening 12, as is the sphere itself. Accordingly, also at this part of the surface the effect of the Ulbricht-sphere occurs.

Finally, a user control device not shown is provided at this cover at the height of the illumination means 1 which comprises a LCD display. This user control device controls a not shown control electronic of the total device and accordingly outputs arithmetically and statistically processed measuring values. It goes without saying that the detectors for determining these measuring values may be read out in a way adapted to the modulation by the chopper aperture 17.

The function of device is as follows:

The sample is inserted into the sample space and the light source is activated. The light passes through the sample and enters the sphere. The first measurement is conducted with closed cover area. The light introduced into the sphere is in total reflected from the surface of the sphere, and the quantity of light detected by the third detector is a measure of the total incident quantity of light and therewith a measure for the total transmission.

Thereafter the cover area is opened, the sample means continously illuminated. The signal of the three detectors is detected and analyzed in the previously described manner.

Thus, it is possible to detect the essential optical characteristic quantities of a transparent sample using only one measuring device and conducting two shortly successive measurements.

In the illustrated embodiment two sample positions are provided. The first position is defined by the annex area 11 at the light outlet opening 10 of the illumination means. The sample is put to this area and then exhibits the maximum possible distance to the detectors. The detectors are arranged such that the angle deviation of 2.5° may be achieved in this position. This means that the distance of the detectors and also the size of the Ulbricht-sphere may be kept relatively small.

The second sample position is defined by the annex at the annex area 13 of the Ulbricht-sphere.

As detectors of the measuring device all kinds of photoelectric devices as photocells, phototransistors etc. may be applied. Preferably photoelectric devices are used which are sensitive over the whole or substantially the whole wavelength range of visible light.

In another preferred embodiment of the previously described embodiment three respective detector elements which exhibit a different wavelength characteristic are used as detector 4, and/or a detector 5 and/or detector 7. Thus, it is also possible to detect the color characteristic of the transmitted light. When using a lamp having defined light as light source 25 it is possible to conduct a quantitatively correct determination of the color behavior.

Most preferably in this case three or more sensors having different wavelength characteristics are used as sensor 6,  because here the spatial arrangement of a plurality of sensors is not a problem.

Alternatively in this embodiment also three or more light sources exhibiting a different wavelength characteristic, such as three light emitting diodes having different colors, may be used instead of the light source 25. In this case it is not necessary to use detectors having different wavelength characteristics, but in three successive measurements involving a respective of the light diodes as light source the color characteristic of the sample may be determined.

Alternatively, both light sources having different wavelength characteristics and detectors having different wavelength characteristics and a combination thereof may be used. In this case it is possible to make a statement about the spectral transmission behavior after an appropriate mathematical analysis.

We claim:

1. A device for measuring characteristic quantities of an at least partially transparent sample, comprising:

means for illuminating the sample, the illumination means including a light source which emits light in a predetermined wavelength range and which is arranged such within the illumination means so that the light substantially propagates along a predetermined optical axis; and means for measuring characteristics of the sample;

wherein the illumination means and the measuring means define a sample reception space, the sample reception space being arranged with respect to the optical axis so that the light which emerges from the light source first passes through the sample located within the sample reception space and then enters the measuring means, the measuring means including a substantially closed measuring space having an inner surface and an opening through which the optical axis extends and through which the light enters after having passed through the sample, the measuring means having a photodetection means being sensitive at least within the predetermined wavelength range, and including a first detector, a second detector and a third detector, the first detector being arranged in the optical axis of the illumination means, the second detector being arranged in a predetermined radial distance from the optical axis, and the third detector being arranged in the measuring space at a distance from the optical axis and directed so that it substantially detects only light reflected from the inner surface of the measuring space which corresponds to a haze value.

2. A device for measuring characteristic quantities of an at least partially transparent sample, comprising:

means for illuminating the sample, the illumination means including a light source which emits light in a predetermined wavelength range and which is arranged such within the illumination means so that the light substantially propagates along a predetermined optical axis; and means for measuring characteristics of the sample;

wherein the illumination means and the measuring means define a sample reception space, the sample reception space being arranged with respect to the optical axis so that the light which emerges from the light source first passes through the sample located within the sample reception space and then enters the measuring means, the measuring means including a substantially closed measuring space having an inner surface and an opening through which the optical axis extends and through which the light enters after having passed through the sample, the measuring means having a photodetection means being sensitive at least within the predetermined wavelength range, a first detector, a second detector and a third detector, the first detector being arranged in the optical axis of the illumination means to detect a direct light transmission value, the second detector being arranged in a predetermined radial distance from the optical axis to detect a clarity value, and the third detector being arranged in the measuring space at a distance from the optical axis to detect substantially only light reflected from the inner surface of the measuring space which corresponds to a haze value.

3. The device according to claim 1, further comprising means positioned within the measuring space for covering the first and second detectors such that the third detector detects the light which is reflected from the surface of the measuring space and from the cover means.

4. The device according to claim 1 or 2, wherein the measuring space has an inner surface, and wherein the inner surface of the measuring space is substantially spherically formed so that the measuring space forms an Ulbricht-sphere.

5. The device according to claim 4, wherein the optical axis intersects the center of the substantially spherical inner surface of the measuring space.

6. The device according to claim 4, wherein the illumination means and the Ulbricht sphere are attached to a common base plate substantially running in parallel to the optical axis via a column.

7. The device according to claim 1, wherein the first detector comprises a substantially planar measuring area, which is inclined with respect to the optical axis so as to obliquely reflect a reflected fraction of an impinging light beam with respect to the optical axis and optionally onto a light absorbing wall.

8. The device according to claim 1 or 2, wherein at least the second detector is separated from the measuring space by a channel, the channel is of an extent that when parallel to the optical axis is relatively large and in a plane parallel to the vertical axis is relatively small, so that the fraction of the light reflected back from the second detector into the measuring space is small.

9. The device according to claim 1 or 2, further comprising means for modulating light beams in the illumination means.

10. The device according to claim 9, wherein the modulation means comprises a chopper aperture.

11. The device according to claim 1 or 2, further comprising means for measuring a reference beam of the illumination means.

12. The device according to claim 11, wherein the reference measuring means is provided at the illumination means.

13. The device according to claim 1, wherein the reference measuring means comprises a partially transparent mirror.

14. The device according to claim 1 or 2, wherein the distance which the second detector exhibits from the optical axis is allocated such that the second detector detects an angle deviation of the light caused by a sample located in the sample reception space which is smaller than 5°.

15. The device according to claim 1 or 2, wherein at least one detector comprises at least two light sensitive areas exhibiting different spectral characteristics.

16. The device according to claim 1 or 2, wherein the illumination means has at least two kinds of light exhibiting different spectral characteristics successively emitted.

17. A device for measuring characteristic quantities of an at least partially transparent sample, comprising:

means for illuminating the sample, the illumination means including a light source which emits light in a predetermined wavelength range and which is arranged such within the illumination means so that the light substantially propagates along a predetermined optical axis; and means for measuring characteristics of the sample;

wherein the illumination means and the measuring means define a sample reception space, the sample reception space being arranged with respect to the optical axis so that the light which emerges from the light source first passes through the sample located within the sample reception space and then enters the measuring means, the measuring means including a substantially closed measuring space having an inner surface an opening through which the optical axis extends and through which the light enters after having passed through the sample, the measuring means having a photodetection means being sensitive at least within the predetermined wavelength range, a first detector and a second detector, the first detector being arranged in the optical axis of the illumination means and the second detector being arranged in a predetermined radial distance from the optical axis, and wherein the first detector includes a substantially planar light sensitive area which is designed substantially in the form of a circle and the second detector includes a substantially planar light sensitive area which is designed substantially in the form of a circular ring, the substantially light sensitive area of the first detector being arranged within the substantially circular ring light sensitive area of the second detector.

18. A device for measuring characteristic quantities of an at least partially transparent sample, comprising:

means for illuminating the sample, the illumination means including a light source which emits light in a predetermined wavelength range and which is arranged such within the illumination means so that the light substantially propagates along a predetermined optical axis; and means for measuring characteristics of the sample;

wherein the illumination means and the measuring means define a sample reception space, the sample reception space being arranged with respect to the optical axis so that the light which emerges from the light source first passes through the sample located within the sample reception space and then enters the measuring means, the measuring means including a substantially closed measuring space having an opening through which the optical axis extends and through which the light enters after having passed through the sample, the measuring space having an inner surface, wherein the inner surface of the measuring space is substantially spherically formed so that the measuring space forms an Ulbricht-sphere, the measuring means having a photodetection means being sensitive at least within the predetermined wavelength range, a first detector, a second detector and a third detector, the first detector being arranged in the optical axis of the illumination means, the second detector being arranged in a predetermined radial distance from the optical axis, and the third detector being arranged in the measuring space at a distance from the optical axis and directed so that it substantially detects only light reflected from the inner surface of the measuring space which corresponds to a haze value.

* * * * *